(12) United States Patent
Banerjee et al.

(10) Patent No.: US 10,336,715 B2
(45) Date of Patent: Jul. 2, 2019

(54) PHOSPHORIC ACID LOADED COVALENT ORGANIC FRAMEWORK AND A PROCESS FOR THE PREPARATION THEREOF

(71) Applicant: Council of Scientific & Industrial Research, New Delhi (IN)

(72) Inventors: Rahul Banerjee, Maharashtra (IN); Suman Chandra, Maharashtra (IN); Tanay Kundu, Maharashtra (IN); Sharath Kandambeth, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 15/689,419

(22) Filed: Aug. 29, 2017

(65) Prior Publication Data

US 2017/0362190 A1    Dec. 21, 2017

Related U.S. Application Data

(62) Division of application No. 14/693,106, filed on Apr. 22, 2015, now Pat. No. 9,758,493.

(30) Foreign Application Priority Data

May 9, 2014    (IN) .......................... 1251/DEL/2014

(51) Int. Cl.
    *C07D 259/00*    (2006.01)
(52) U.S. Cl.
    CPC ................................. *C07D 259/00* (2013.01)
(58) Field of Classification Search
    None
    See application file for complete search history.

(56) References Cited

PUBLICATIONS

Chandra et al., Phosphoric Acid Loaded Azo (–N=N–) Based Covalent Organic Framework for Proton Conduction. Journal of American Chemical Society, 2014, 136, 6570-6573 and its supporting information.*
Chemical Abstract Registry No. 72970-56-0, indexed in the Registry File on STN CAS Online Nov. 16, 1984.

* cited by examiner

*Primary Examiner* — Po-Chih Chen
(74) *Attorney, Agent, or Firm* — Wood Herron & Evans LLP

(57) ABSTRACT

The present invention is directed to a process for the preparation of phosphoric acid loaded covalent organic framework (PA@Tp-Azo and PA@Tp-Stb) with high stability and high proton conductivity.

5 Claims, 17 Drawing Sheets

PHOSPHORIC ACID LOADED COVALENT ORGANIC FRAMEWORK AND A PROCESS FOR THE PREPARATION THEREOF

CROSS-REFERENCE TO RELATED APPLICATIONS

The present application is a Divisional application of U.S. Ser. No. 14/693,106, filed Apr. 22, 2015, which claims priority under 35 U.S.C. § 119 of Indian Patent Application No. 1251/DEL/2014, filed May 9, 2014, the disclosures of which are hereby expressly incorporated by reference herein in their entireties.

FIELD OF THE INVENTION

The present invention relates to phosphoric acid loaded covalent organic framework for proton conduction. Particularly, the present invention relates to preparation of chemically stable azo-based Covalent Organic Framework and a process for the preparation of phosphoric acid loaded covalent organic framework with high proton conductivity.

BACKGROUND OF THE INVENTION

Covalent Organic Frameworks (COFs) are three dimensional crystalline materials prepared by linking lighter elements (e.g., B, C, N, O) via covalent bonds in a periodic manner. COFs are typically synthesized and subsequently crystallized by means of reversible condensation reactions/covalent bond formation reactions like boronic acid trimerisation, boronate ester formation and Schiff base reaction. Structurally, COFs are closely related to metal-organic frameworks (MOFs), where coordination bonds link metal ions and organic struts. Metal-organic frameworks (MOFs) can facilitate proton conduction by accommodating guest molecules, such as water and imidazole, in well-defined pores or integrating functional acidic groups onto the channel walls. Although COFs have shown excellent promise as semiconductive device, sensors, in gas storage and in separation, but proton conductivity in COFs are still unprecedented. Structurally, COFs are closely related to metal-organic frameworks (MOFs), where coordination bonds link metal ions and organic struts. Although COFs have shown excellent promise as semiconductive devices, sensors and in gas storage and separation proton conductivity in COFs is still unexplored.

In recent years, proton conducting materials have gathered remarkable interest among researchers due to their application in fuel cells, sensors and electronic devices, refer, (a) Mauritz, K. A.; Moore, R. B. Chem. Rev. 2004, 104, 4535 and (b). Hickner, M.; Ghassemi, H.; Kim, Y. S.; Einsla, B. R.; McGrath, J. E. Chem. Rev. 2004, 104, 4587. Nafion based proton conducting membranes are considered as the benchmark in this field which exhibit high proton conductivity (ca. $10^{-1}$ Scm$^{-1}$) at moderate temperature (60° C.-80° C.) under high relative humidity (98% RH), refer Paddison, S. J. Annu. Rev. Mater. Res. 2003, 33, 289. However, high cost of Nafion, (perfluorinated membranes) with less efficiency at fuel cell operating temperature (120° C.) always encouraged researchers to search for alternative materials. In this context, MOFs with loaded carrier molecules (e.g., imidazole, triazole, mineral acids) has been envisaged for high temperature proton conduction applications and several references are available for the same. However, these MOFs suffer poor hydrolytic stability with very low pH tolerance of the occluded guests. As a result, rupture of the coordination bonds and the framework backbone occurs, which limits its applicability in fuel cell operating conditions. In addition, high gravimetric weight of MOF, difficulty in forming compact membrane and its stability at higher temperatures are necessary to consider for future development of proton conducting materials.

Article titled "Proton-conducting membranes based on benzimidazole polymers for high-temperature PEM fuel cells. A chemical quest" by J A Asensio et al. published in *Chem. Soc. Rev.*, 2010, 39, pp 3210-3239 reports Proton-conducting membranes based on benzimidazole polymers for high-temperature PEM fuel cells. They also reports Acid-impregnated polybenzimdazole type membranes with high thermal stability after PA loading. However, lack of crystallinity of polymeric membranes results in limitations such as multidirectional hopping of protons which affect the proton transport rate and insufficient mechanistic insight of the transport mechanism limit further improvement of the material.

Article titled "Chemically stable multilayered covalent organic nanosheets from covalent organic frameworks via mechanical delamination" by S Chandra et al. published in *J. Am. Chem. Soc.*, 2013, 135 (47), pp 17853-17861 reports a series of five thermally and chemically stable functionalized covalent organic frameworks (COFs), namely, TpPa-N$O_2$, TpPa-F$_4$, TpBD-(NO$_2$)$_2$, TpBD-Me$_2$, and TpBD-(OMe)$_2$ synthesized by solvothermal aldehyde-amine Schiff base condensation reaction.

Article titled "Construction of crystalline 2d covalent organic frameworks with remarkable chemical (acid/base) stability via a combined reversible and irreversible route" by S Kandambeth et al. published in *J. Am. Chem. Soc.*, 2012, 134 (48), pp 19524-19527 reports two new chemically stable [acid and base] 2D crystalline covalent organic frameworks (COFs) (TpPa-1 and TpPa-2) synthesized using combined reversible and irreversible organic reactions. Synthesis of TpPa-1 and TpPa-2 COFs was done by the Schiff base reactions of 1,3,5-triformylphloroglucinol (Tp) with p-phenylenediamine (Pa-1) and 2,5-dimethyl-p-phenylenediamine (Pa-2), respectively, in 1:1 mesitylene/dioxane.

PCT application No. 2014057504 discloses covalent organic frameworks (COFs) which exhibit stability towards acidic, basic and neutral conditions and process for the synthesis thereof. Also, the invention provides an environmentally-friendly mechanochemical/solvothermal process for the construction of stable covalent organic frameworks (COFs) efficiently at a faster rate and in high yield.

Article titled "Imparting High Proton Conductivity to a Metal-Organic Framework Material by Controlled Acid Impregnation" by V G Ponomareva et al. published in *J. Am. Chem. Soc.*, 2012, 134 (38), pp 15640-15643 reports the impregnation of the mesoporous metal-organic framework (MOF) MIL-101 by nonvolatile acids $H_2SO_4$ and $H_3PO_4$ to affords solid materials with potent proton-conducting properties at moderate temperatures, which is critically important for the proper function of on-board automobile fuel cells.

Article titled "Proton conductivity of phosphoric acid doped polybenzimidazole and its composites with inorganic proton conductors" by R He et al. published in *Journal of Membrane Science*, 1 Dec. 2003, 226 (1-2), pp 169-184 reports phosphoric acid doped polybenzimidazole (PBI) and PBI composite membranes. They also reports that the conductivity of phosphoric acid doped PBI and PBI composite membranes is dependent on the acid doping level, relative humidity (RH) and temperature.

The qualities of COFs such as light weight in nature, wide variety of functionality, thermal stability and membrane processability like polymers, ensure its sustainability in harsh fuel cell operating conditions and high degree of internal ordering like MOFs, enable loading and transport of proton conducting substrates. Despite the above promising features, COFs have never been tested for proton conduction due to their instability in ambient humidity conditions.

Therefore, there is an unmet need in the art to develop COFs with greater stability under ambient conditions, so as to increase their applications in proton conduction.

OBJECTIVE OF THE INVENTION

The main objective of present invention is to provide phosphoric acid loaded covalent organic framework with high stability and high proton conductivity.

Another objective of present invention is to provide a stable loaded covalent organic framework which shows greater stability under ambient conditions as well as towards strong acidic and moderately strong basic conditions even upon isoreticulation and functionalization.

Yet another object of the present invention is to provide a process for the preparation of phosphoric acid loaded covalent organic framework with high stability and high proton conductivity.

SUMMARY OF THE INVENTION

Accordingly, the present invention provides a phosphoric acid loaded covalent organic framework comprising phosphoric acid (PA) in the range of 2 to 6 (wt %) and covalent organic framework in the range of 94 to 98 (wt %) wherein covalent organic framework are selected from Tp(1,3,5-triformylphloroglucinol)-Azo (4,4'-azodianiline) or Tp-Stb (4,4-diaminostilbene).

In an embodiment of the present invention, proton conductivity of phosphoric acid loaded covalent organic framework (PA@Tp-Azo) is $9.9 \times 10^{-4}$ s/cm at 332K in 98% RH.

In another embodiment of the present invention, proton conductivity of phosphoric acid loaded covalent organic framework (PA@Tp-Azo) is $6.7 \times 10^{-5}$ s/cm at 340K in 0% relative humidity (RH).

In yet another embodiment of the present invention, proton conductivity of phosphoric acid loaded covalent organic framework (PA@Tp-Stb) is $2.3 \times 10^{-5}$ s/cm at 332K in 98% relative humidity (RH).

In yet another embodiment, present invention provides a process for preparing phosphoric acid loaded covalent organic framework with high stability and high proton conductivity comprising the steps of:

a) dispersing 1,3,5-triformylphloroglucinol (Tp) and diamine compound in solvent by ultrasonication for 10 minutes followed by degassing the solution;

b) heating the solution as obtained in step (a) in oven for 3-5 days at temperature in the range of 100° C. to 120° C. followed by washing and drying under vacuum at temperature in the range of 120° C. to 150° C. for period in the range of 12 h to 18 h to obtain desired covalent organic framework with at least one basic anchoring site;

c) immersing the covalent organic framework material of step (b) in $H_3PO_4$ for period in the range of 1 h to 5 h followed by washing to remove the surface absorbed phosphoric acid and activating overnight for period in the range of 12 h to 18 h at temperature in the range of 60° C. to 80° C. under vacuum to obtain phosphoric acid loaded covalent organic framework.

In yet another embodiment of the present invention, the diamine compound in step (a) is 4,4'-azodianiline (Azo) or 4,4-diaminostilbene (Stb) dihydrochloride.

In yet another embodiment of the present invention, the covalent organic framework formed in step (b) is Tp-Azo or Tp-Stb.

In yet another embodiment of the present invention, phosphoric acid loaded covalent organic framework formed in step (c) is PA@Tp-Azo or PA@Tp-Stb.

In yet another embodiment of the present invention, the solvent used in step (a) is mixture of dimethylacetamide and o-dichlorobenzene in 1:1 ratio.

ABBREVIATIONS USED

COF—Covalent organic framework
PA@Tp-Azo—phosphoric acid loaded azo based (—N=N—) covalent organic framework
PA@Tp-Stb—phosphoric acid loaded ethylene based (—CH=CH—) covalent organic framework

DETAILED DESCRIPTION OF THE INVENTION

One aspect of the present invention is to provide a stable loaded covalent organic framework which shows greater stability under ambient conditions as well as towards strong acidic and moderately strong basic conditions even upon isoreticulation and functionalization.

Another aspect of the present invention is to provide a process for the preparation of phosphoric acid loaded covalent organic framework with high stability and high proton conductivity comprising the steps of:

a) dispersing 1,3,5-triformylphloroglucinol and diamine compound in solvent by ultrasonication for 10 minutes followed by degassing the solution through three freeze-pump-thaw cycles;

b) heating of the solution of step (a) in oven for 3 days at 120° C. followed by washing the COFs until it is pure and then drying under vacuum at 150° C. for 12 h to obtain desired covalent organic framework with at least one basic anchoring site;

c) immersing the covalent organic framework material of step (b) in $H_3PO_4$ for 2 h followed by washing to remove the surface absorbed phosphoric acid and activating overnight at 80° C. under vacuum to obtain phosphoric acid loaded covalent organic framework.

The covalent organic framework formed in step (b) is Tp-Azo or Tp-Stb.

The phosphoric acid loaded covalent organic framework formed in step (c) is PA@Tp-Azo or PA@Tp-Stb.

The diamine compound in step (a) is 4,4'-azodianiline or 4,4-diaminostilbene dihydrochloride and the solvent is (1:1) mixture of dimethylacetamide and o-dichlorobenzene.

The covalent organic framework formed in step (b) greater stability under ambient conditions as well as towards strong acidic and moderately strong basic conditions even upon isoreticulation and functionalization.

Figure 1A:
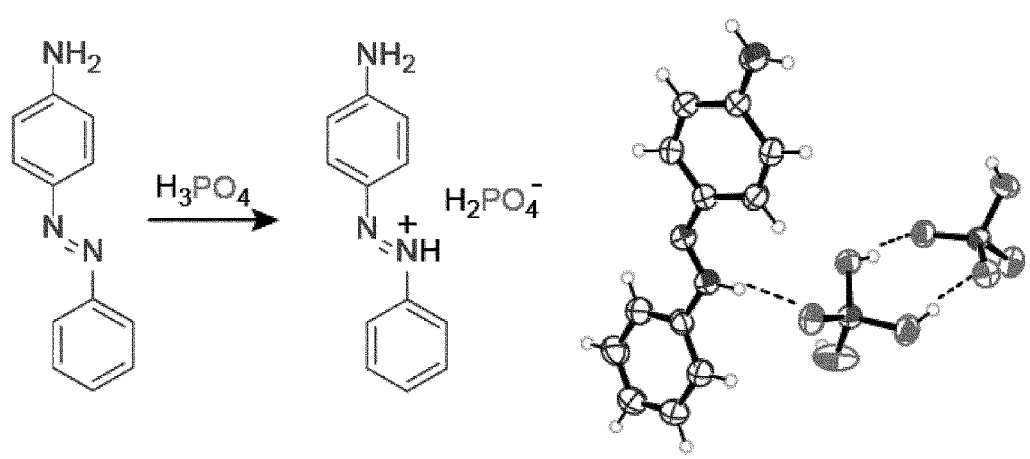
FIG. 1A is a crystal structure of 4-[(E)-phenyl-diazenyl]anilinium dihydrogen phosphate phosphoric acid solvate.
Figure 1B:
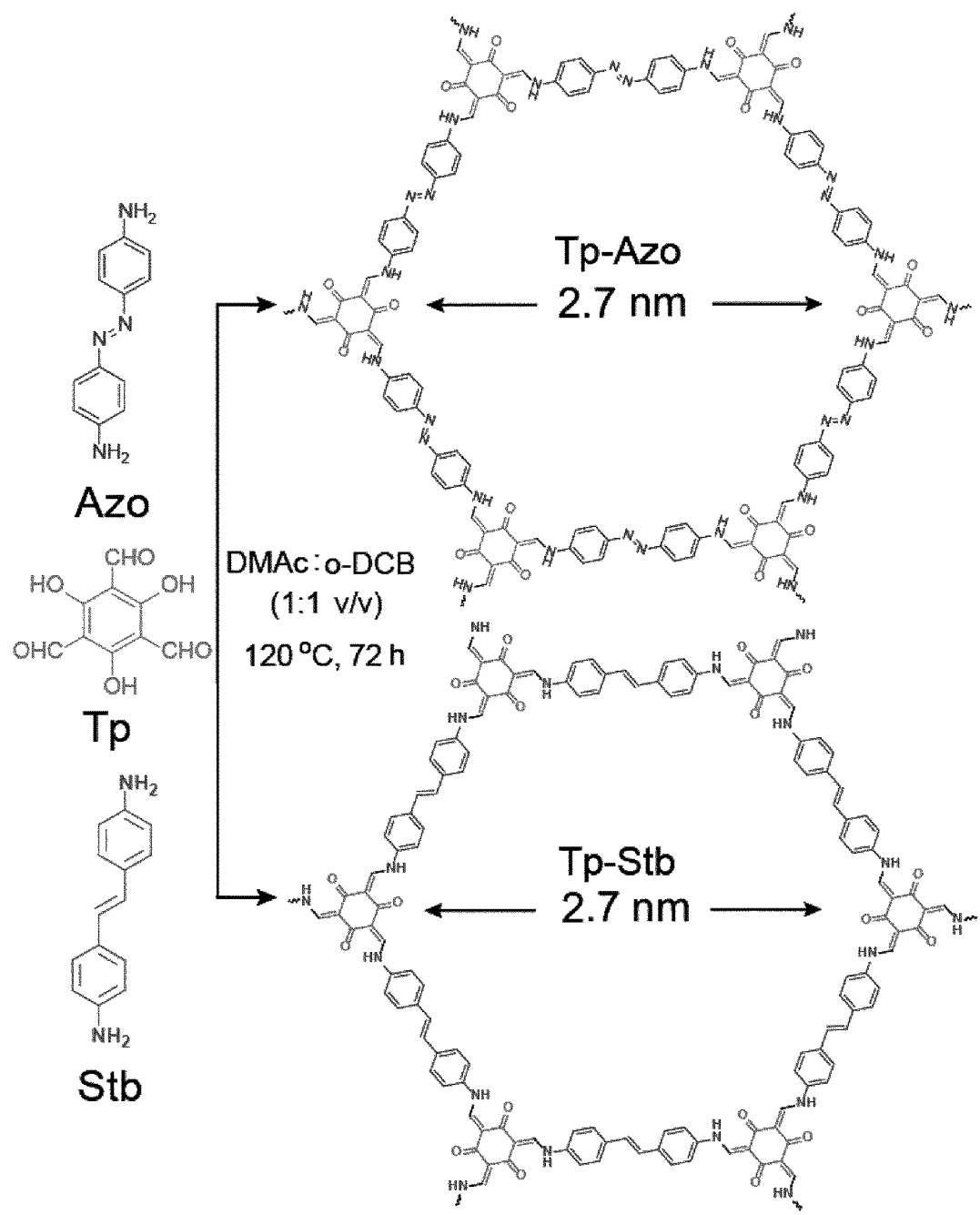
FIG. 1B is a schematic representation of synthesis of Tp-Azo and Tp-Stb by the reaction between 1,3,5-triformylphloroglucinol (Tp) and 4,4'-azodianiline (Azo) or 4,4'-diaminostilbene (Stb), respectively.

The present invention provides azo functionalized COF (Tp-Azo) (FIG. 1B) which are prepared by Schiff base reaction between 1,3,5-triformylphloroglucinol (Tp) and 4,4'-azodianiline (Azo) and exhibit excellent structural stability, porosity and crystallinity even after acid treatment. PA@Tp-Azo of the instant invention shows proton conductivity in both humid and anhydrous conditions ($9.9 \times 10^{-4}$ and $6.7 \times 10^{-5}$ $Scm^{-1}$, respectively). To elucidate the structure-property relationship, the inventors have synthesized the non-azo counterpart, i.e., stilbene functionalized COF (Tp-Stb) (FIG. 1B) which shows less stability, crystallinity, porosity and much less proton conductivity than Tp-Azo because of the nonavailability of anchoring site.

The synthesis of Tp-Azo and Tp-Stb begins by reacting 1,3,5-triformylphloroglucinol with 4,4'-azodianiline or 4,4'-diaminostilbene using an organic solvent. The organic solvent is preferably 1:1 mixture of dimethylacetamide and o-dichlorobenzene as solvent. The reactants were first dispersed in the solvent by ultrasonication for 10 minutes and then degassed through three freeze-pump-thaw cycles. The tubes were then vacuum sealed, placed in isotherm oven for 3 days at 120° C. Finally, the material was filtered out and washed with dry acetone and dried under vacuum at 180° C. for 12 h to obtain Tp-Azo and Tp-Stb respectively.

Figure 3A:
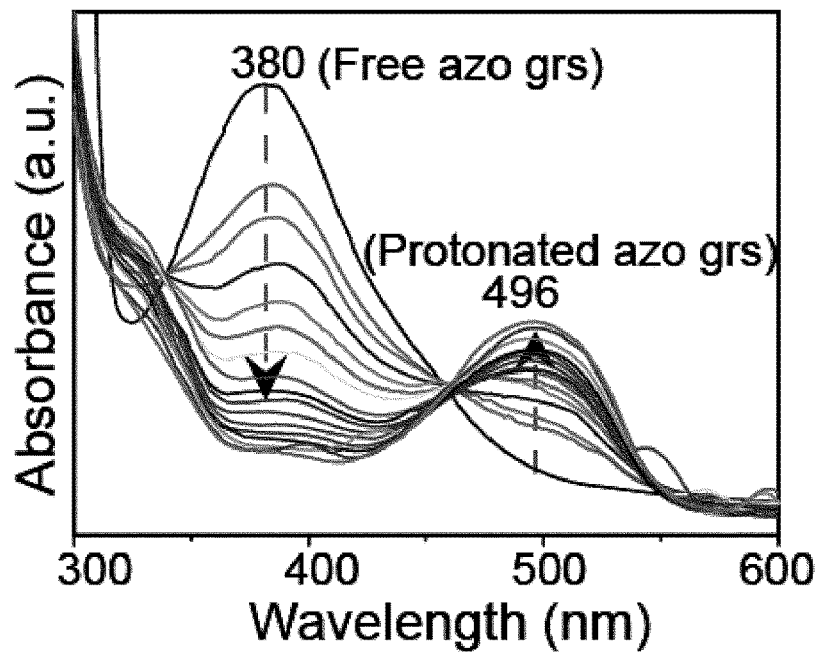
FIG. 3A changes in the UV-Vis spectra of monomer of Tp-Azo with increasing concentration of $H_3PO_4$.
Figure 3B:
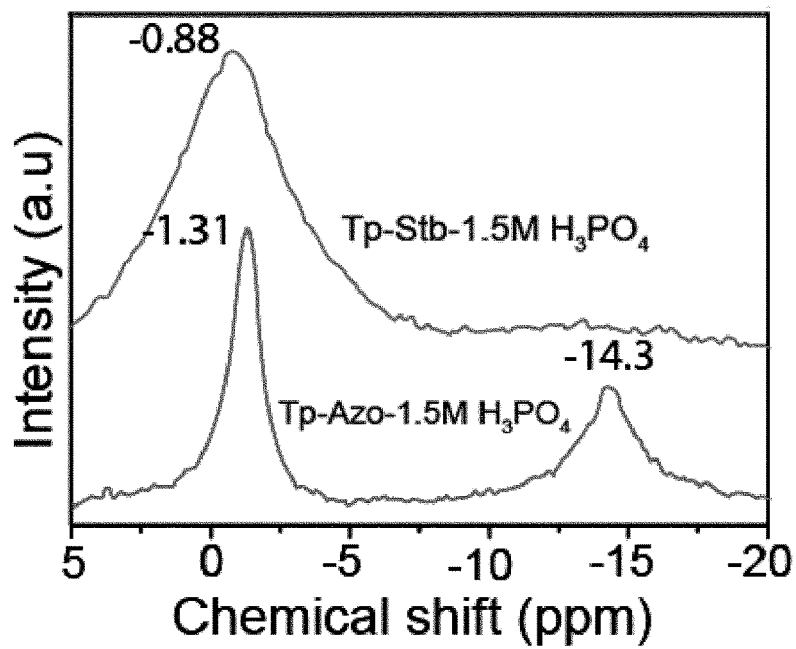
FIG. 3B is $^{31}P$ CP-NMR of $H_3PO_4$ treated Tp-Azo and Tp-Stb.

The PXRD patterns of Tp-Azo and Tp-Stb indicate an intense peak at $2\theta=3.2°$ which corresponds to 100 plane reflections (FIG. 1A), with minor peaks at 5.5, 6.4, 8.4 and 27° (001 plane). The π-π stacking distance between COF layers was calculated as 3.4 Å from the d spacing between 001 planes. In order to elucidate the structure of these COFs and to calculate the unit cell parameters, a possible 2D model was built with eclipsed structure in hexagonal space group (P6/m) and staggered structure in P1 space group using the software Crystal 09. The experimental PXRD pattern matches well with the simulated pattern of the eclipsed stacking model (FIG. 3A). The unit cell values were found to be (a=b=31.5 Å, c=3.3 Å) for Tp-Azo and (a=b=30.500 Å, c=3.49 Å) for Tp-Stb.

Figure 2A:
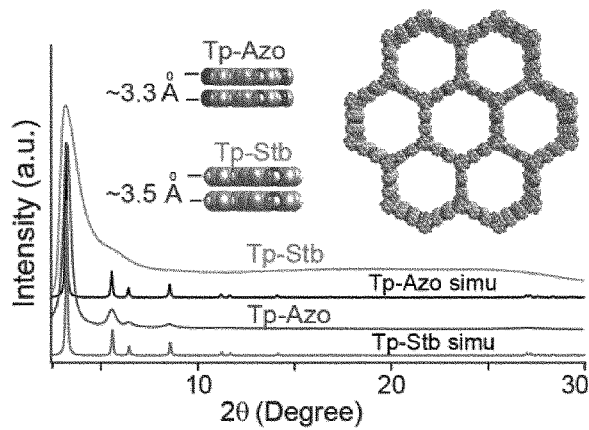
FIG. 2A is observed PXRD patterns of Tp-Azo (Blue) and Tp-Stb (Green) compared with simulated patterns.
Figure 2B:
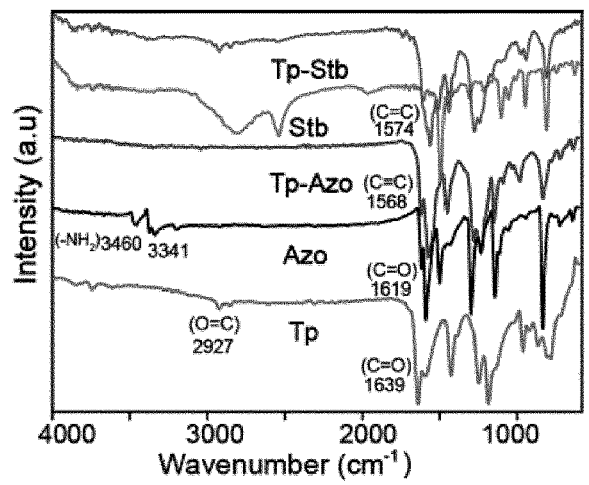
FIG. 2B is a FT-IR spectra of Tp-Azo and Tp-Stb compared with starting material Tp, Azo and Stb.
Figure 2C:
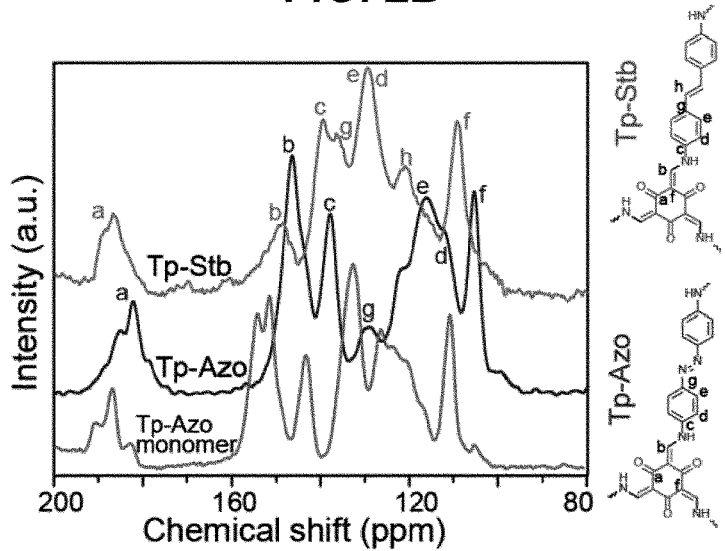
FIG. 2C is a $^{13}C$ NMR comparison of Tp-Azo (Blue), Tp-Stb (Green) compared against the reference compound Tp-Azo monomer=2,4,6-tris(((4-((E)-phenyldiazenyl)phenyl)amino)methylene)cyclohexane-1,3,5-trione (Red)
Figure 3C:
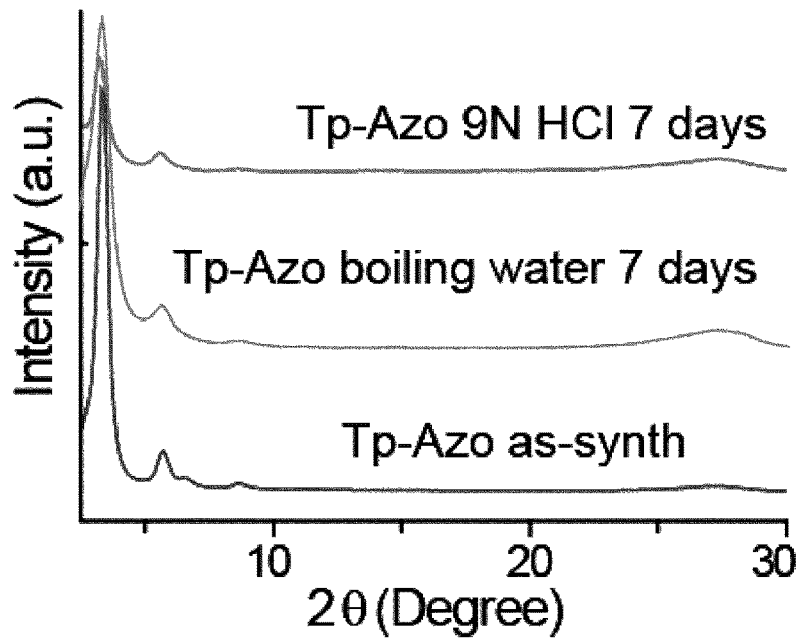
FIG. 3C is PXRD patterns of HCl (Red), boiling water (Orange) treated and as-synthesized Tp-Azo (Blue)
Figure 4A:
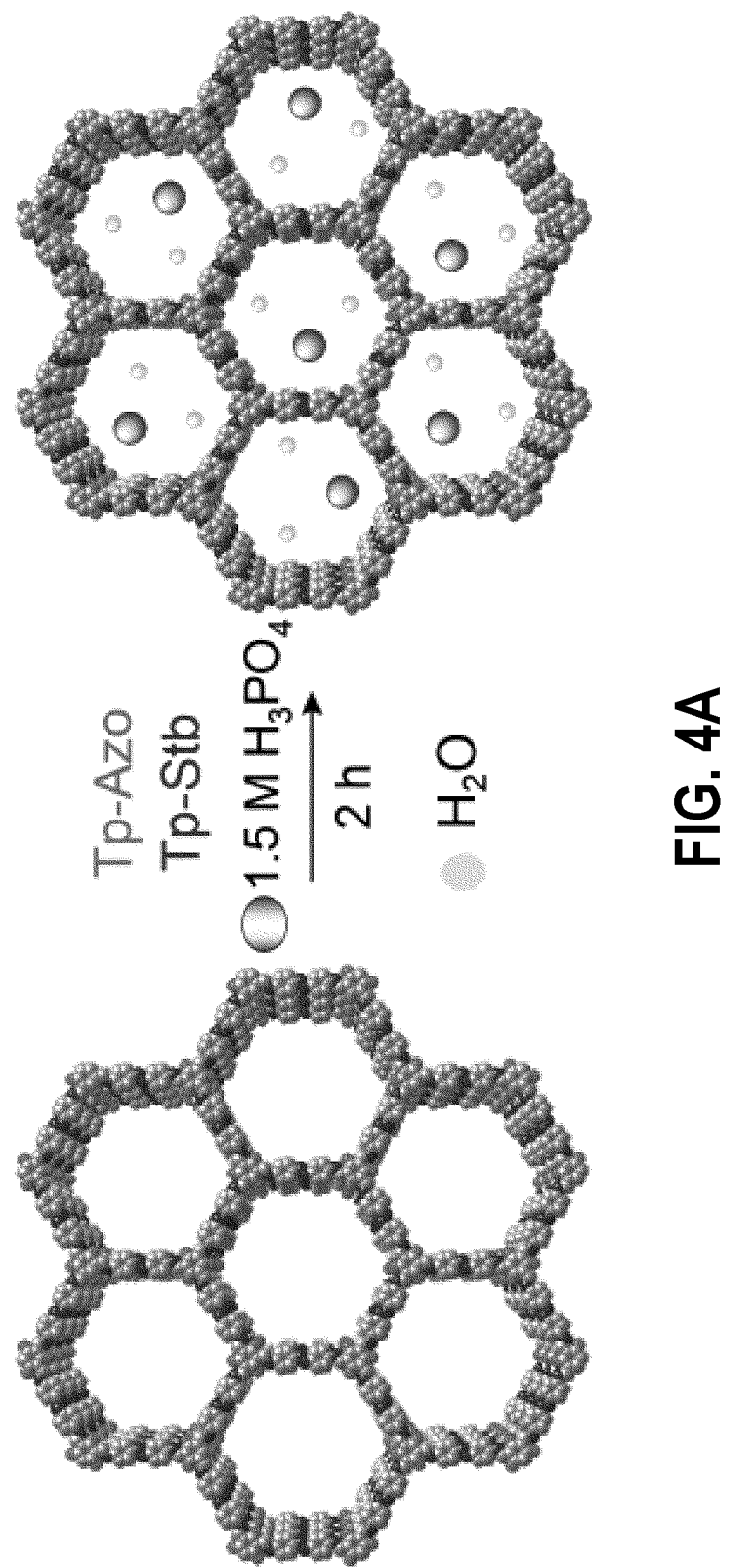
FIG. 4A is a schematic representation of $H_3PO_4$ doping in COFs.
Figure 4C:
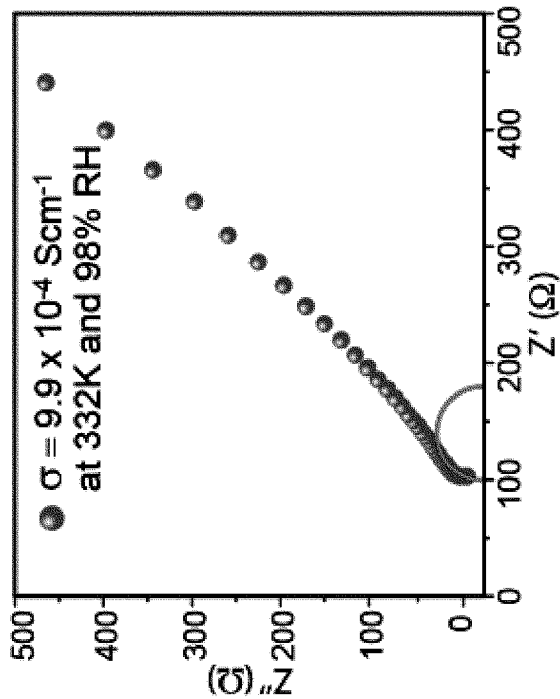
FIG. 4C is hydrous condition.
Figure 4B:
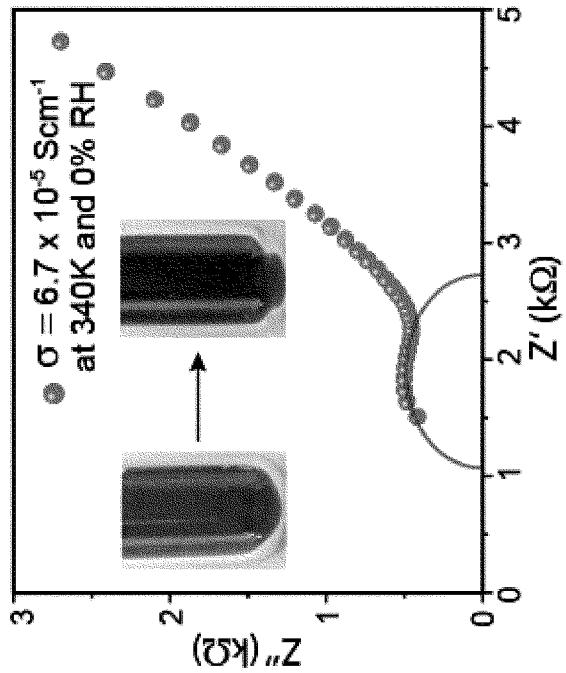
FIG. 4B is proton conductivity of PA@Tp-Azo in anhydrous condition.
Figure 4E:
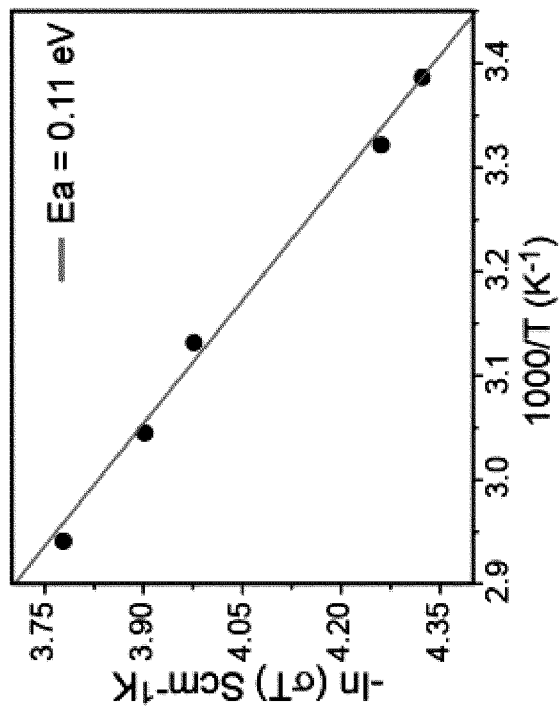
FIG. 4E is activation energy plot for PA@Tp-Azo in hydrous condition.
Figure 4D:
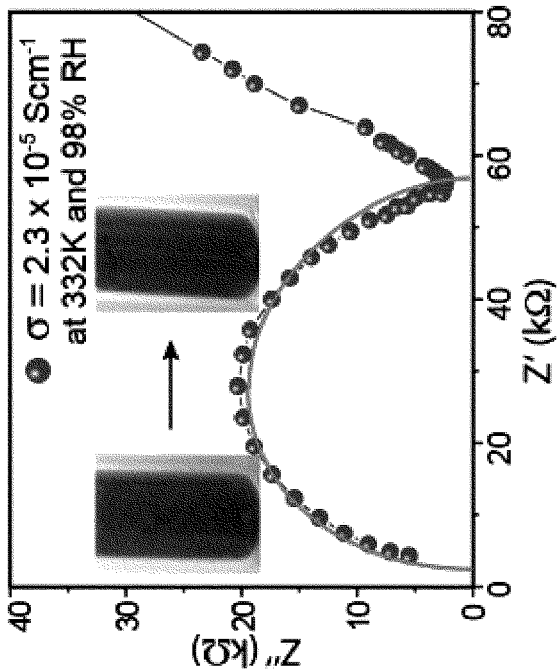
FIG. 4D is proton conductivity of PA@Tp-Stb in hydrous condition.

FT-IR spectra of Tp-Azo and Tp-Stb indicate total consumption of starting materials due to the disappearance of N—H stretching bands (3100-3300 $cm^{-1}$) of Azo or Stb and carbonyl stretching bands (1639 $cm^{-1}$) of Tp (FIG. 2B). Strong peak at 1578 $cm^{-1}$ arises due to the C=C stretching in keto-form similar to the FT-IR spectrum of the reference compound 2,4,6-tris((phenyldiazenyl)phenylamino-methylene)cyclohexane-1,3,5-trione, monomer of Tp-Azo [product of the reaction of 1,3,5-triformylphloroglucinol (Tp) and 4-aminoazobenzene]. Most of the FT-IR peaks of Tp-Azo and Tp-Stb match well with that of the reference compound (FIG. 2B). The C=O peaks (1619 $cm^{-1}$) of Tp-Azo and Tp-Stb get merged with C=C stretching band (1582 $cm^{-1}$). The isolation of Tp-Azo and Tp-Stb as keto form was confirmed by $^{13}C$ CP-MAS solid state NMR. Both COFs show carbonyl (C=O) carbon signals at δ=181 and 186 ppm for Tp-Azo and Tp-Stb, respectively. In the starting material, trialdehyde carbonyl (C=O) carbon resonate at a downfield position around δ=192 ppm. The absence of peak at δ=192 ppm in $^{13}C$ CP-NMR spectrum also indicates the total consumption of the starting materials (FIG. 3C). To investigate the protonation of azo bond by phosphoric acid in PA@Tp-Azo, $^{31}P$ CP-NMR was conducted which shows two distinct peaks at δ −1.31 ppm and δ −14.3 ppm. The $^{31}P$ resonance peak at δ −1.31 ppm attribute to the undissociated $H_3PO_4$ and the shoulder at δ −14.3 ppm correspond to the $H_2PO_4^-$ anion which indicate the protonation of azo bond. However in PA@Tp-Stb only single intense peak at δ −0.88 ppm correspond to undissociated $H_3PO_4$ observed and the peak at δ −14.3 ppm was absent which conclude the absence of $H_2PO_4^-$ anion due to the lack of protonation site in Tp-Stb (FIG. 4B).

Figure 3D:
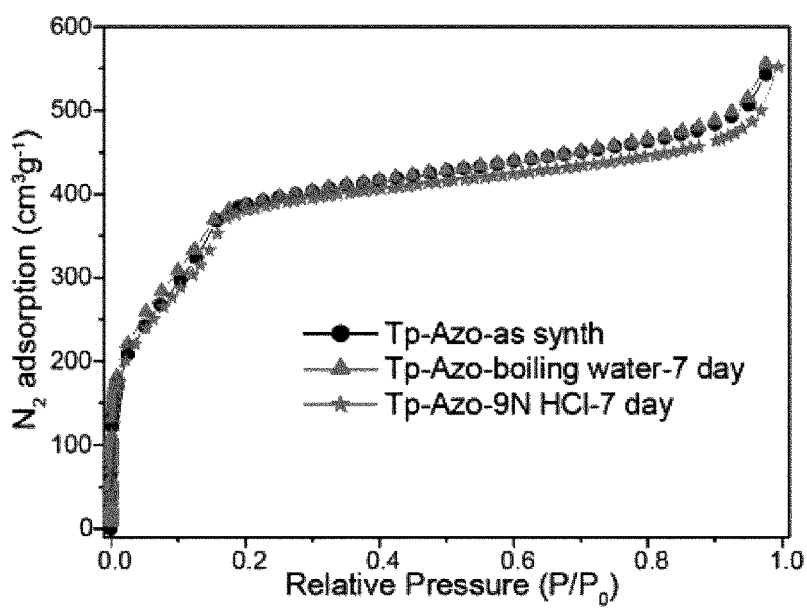
FIG. 3D is $N_2$ adsorption isotherms of Tp-Azo (Blue), boiling water (Orange) and acid treated Tp-Azo (Red)
Figure 3E:
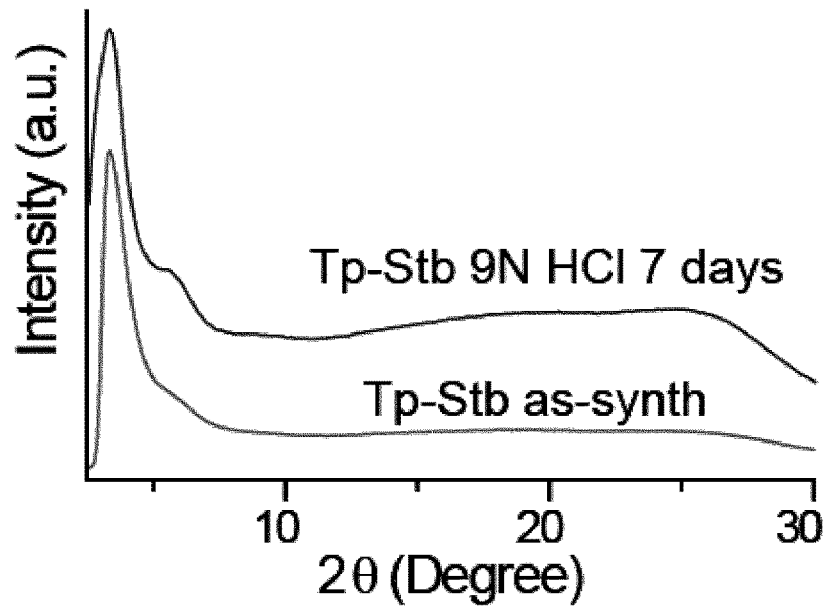
FIG. 3E is PXRD patterns of HCl treated (Blue) and as-synthesized Tp-Stb (Green)
Figure 3F:
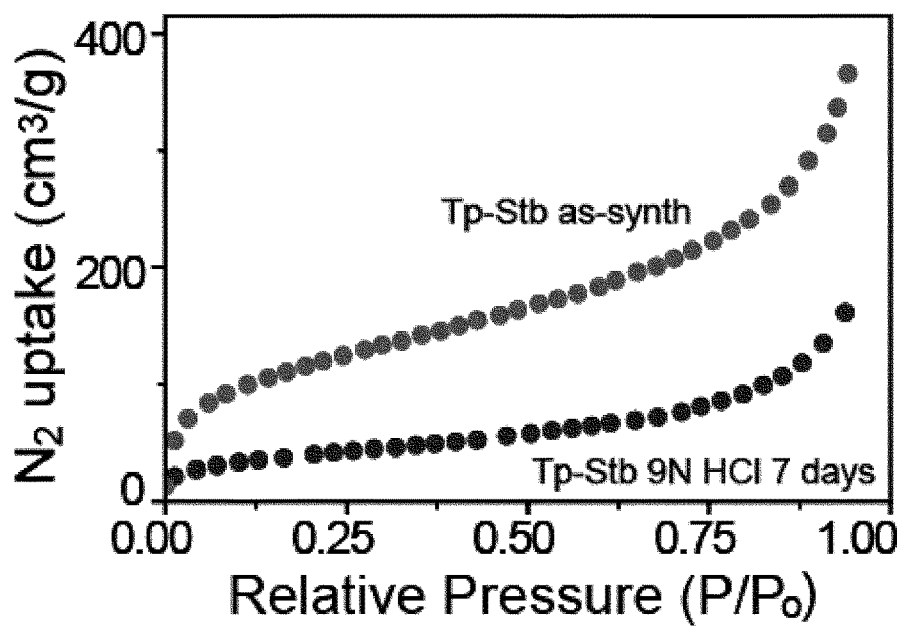
FIG. 3F is $N_2$ adsorption isotherms of as-synthesized Tp-Stb (Green) and 9 N HCl treated Tp-Stb (Blue)

Thermogravimetric analysis (TGA) of the activated Tp-Azo and Tp-Stb show thermal stability up to 350° C., with a gradual weight loss of 50% after 360° C. due to the decomposition of the framework. Permanent porosity of Tp-Azo and Tp-Stb are evaluated by $N_2$ adsorption isotherm at 77 K, which show reversible type IV adsorption isotherm. Surface area of the activated COFs calculated using BET model was found to be 1328 and 422 $m^2/g$ for Tp-Azo and Tp-Stb, respectively (FIGS. 3D and 3F). The lower surface area of Tp-Stb may be due to the poor crystallinity and not so uniform channels resulted from the lower solubility of Stb precursors in organic solvents. Pore size distribution of Tp-Azo and Tp-Stb shows a narrow pore size distribution between the ranges of 1.6-2.5 nm.

The stability of Tp-Azo and Tp-Stb were assayed by immersing 50 mg of COFs in either 20 ml boiling water, or standing in 20 ml strong mineral acids (9 N HCl/1.5 M $H_3PO_4$) and bases (3-6 N NaOH) (FIGS. 11-14). Interestingly, both Tp-Azo and Tp-Stb remain stable, crystalline and porous while directly submerged in boiling water for several days (7 days), as verified by PXRD, FT-IR spectra and $N_2$ adsorption isotherm. Further, these COFs also exhibit strong acid (9 N HCl) stability with almost retention of molecular crystallinity. However, base treated (3-6 N NaOH) COFs show moderate base stability with partial retention of crystallinity. The $N_2$ adsorption isotherm of the 9 N HCl treated Tp-Azo indicates the retention of its intrinsic porosity, while Tp-Stb shows decrease in porosity after the acid treatment. However, 1.5 M $H_3PO_4$ treatment shows significant loss of porosity in both cases, which alludes to $H_3PO_4$ loading. $H_3PO_4$ exhibit high proton conductivity ($10^{-1}$ Scm$^{-1}$) due to its low volatility (>158° C.) and high proton mobility resulted from extended hydrogen bonding utilizing three ionizable O—H bonds. The significant loss of porosity indicates that azo/stilbene groups are susceptible for the protonation and can stabilize the counter anions like phosphate or dihydrogenphosphate.

The PA@Tp-Azo and PA@Tp-Stb covalent organic frameworks are prepared by $H_3PO_4$ loading in Tp-Azo and Tp-Stb (FIG. 4A), which is achieved by simply immersing the evacuated COF materials in 1.5 M $H_3PO_4$ for 2 h. Further, COFs are washed with copious amount of water and activated overnight at 353K under dynamic vacuum to obtain $H_3PO_4$ loaded PA@Tp-Azo and PA@Tp-Stb. It is significant that the $H_3PO_4$ loaded COFs exhibit identical IR spectra and $^{13}C$ NMR spectra along with moderate crystallinity and porosity compared to the parent COFs Tp-Azo and Tp-Stb. Tp-Azo possess a higher acid loading (5.4 wt %) compared to Tp-Stb (2.8 wt %) as evident from TGA analysis.

Figures 8A, 8B:
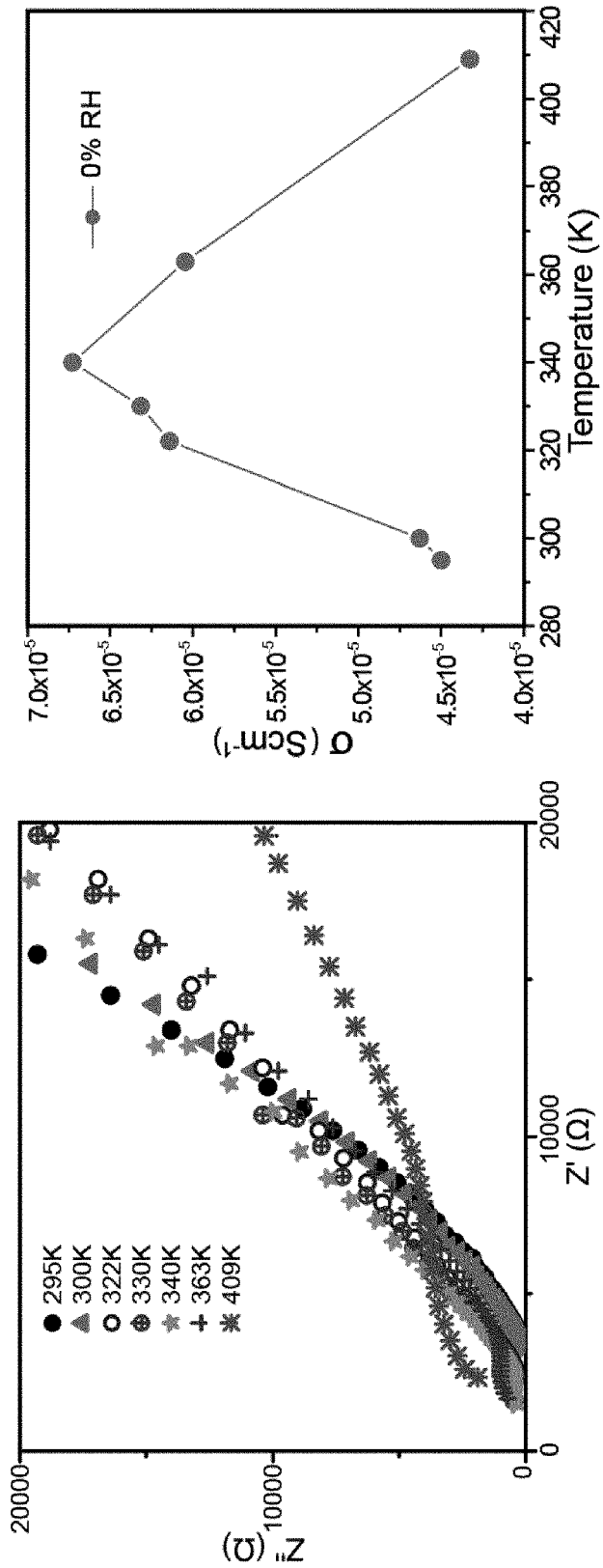
FIG. 8A is Nyquist plots for PA@Tp-Azo in anhydrous condition at different temperatures.
FIG. 8B is a variation of proton conductivity as a function of temperature.
Figures 9A, 9B:
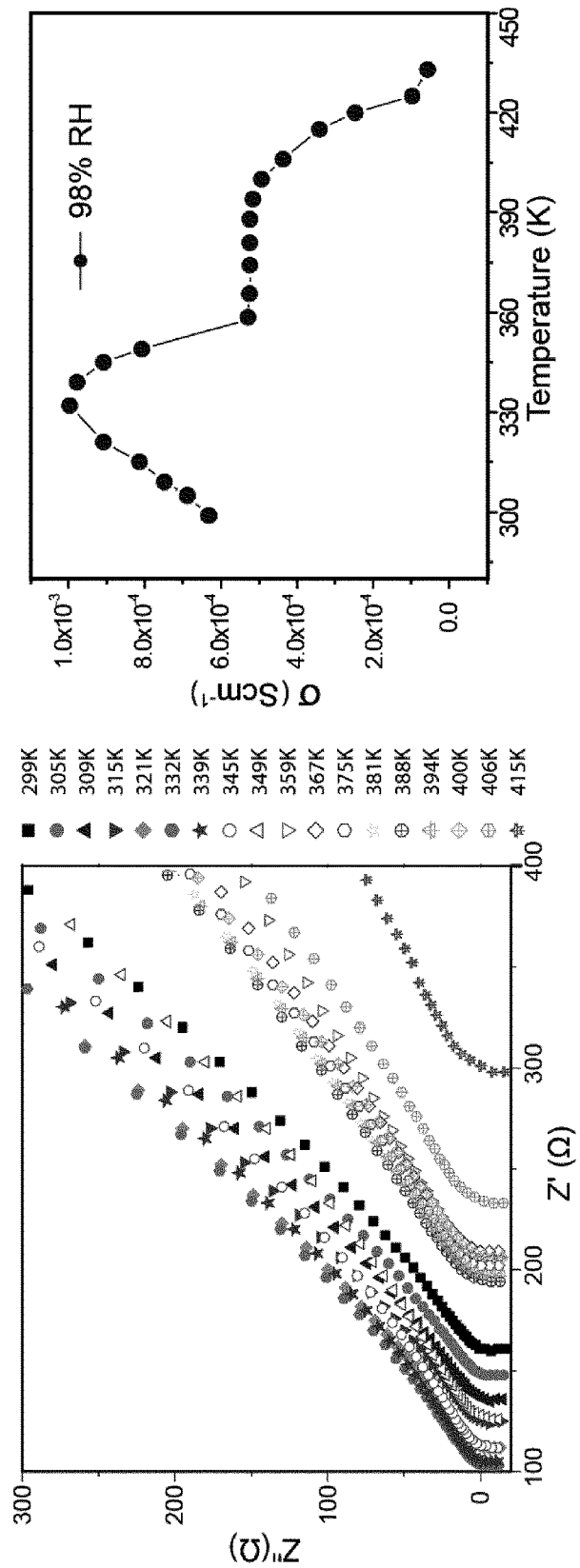
FIG. 9A is Nyquist plots for PA@Tp-Azo in hydrous condition at different temperatures.
FIG. 9B is a variation of proton conductivity as a function of temperature.
Figure 10A:
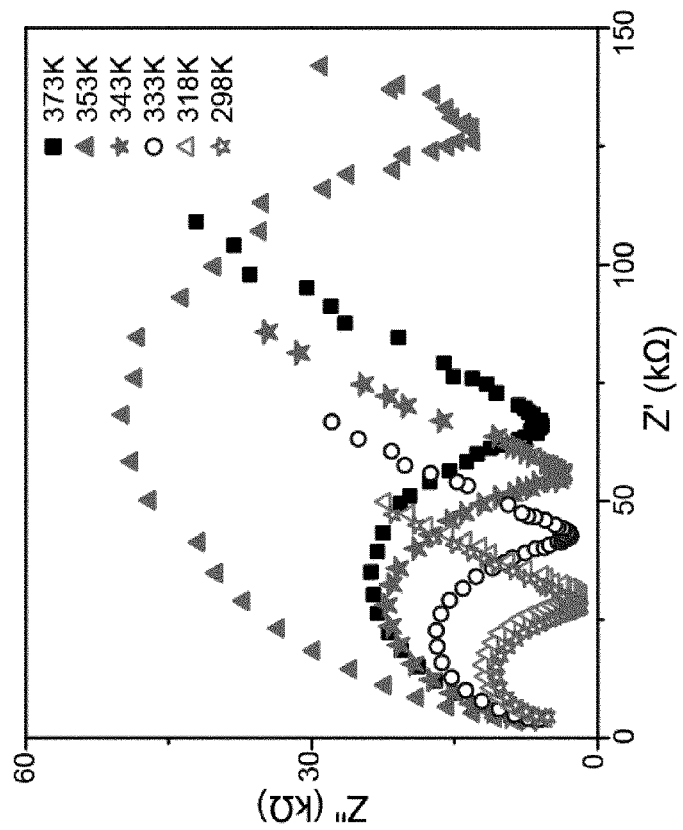
FIG. 10A is selected Nyquist plots for PA@Tp-Stb in hydrous condition at different temperatures.
Figure 10B:
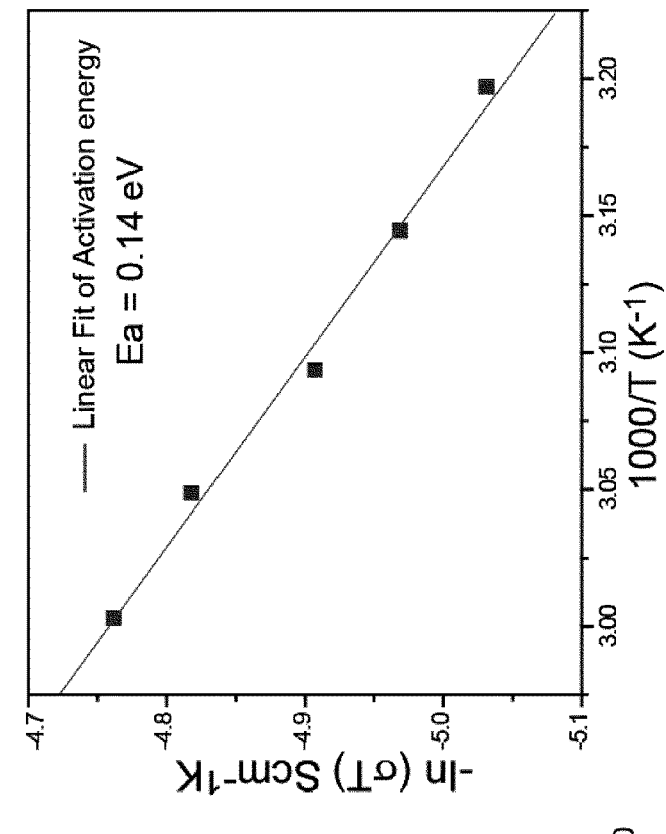
FIG. 10B is activation energy fitting for PA@Tp-Stb.
Figure 11:
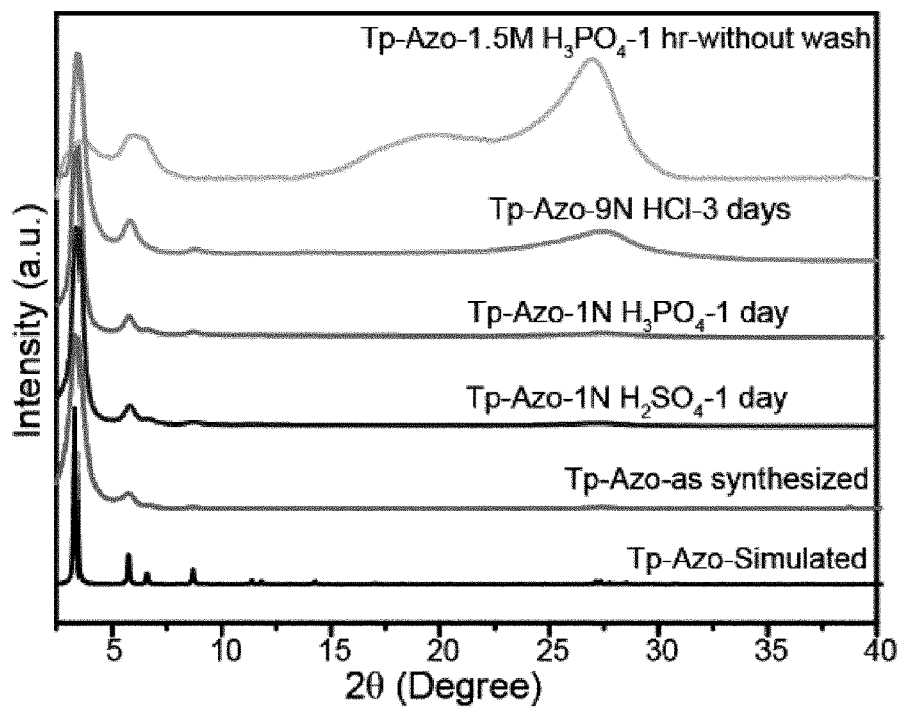
FIG. 11 is stability of Tp-Azo in acid.
Figure 12:
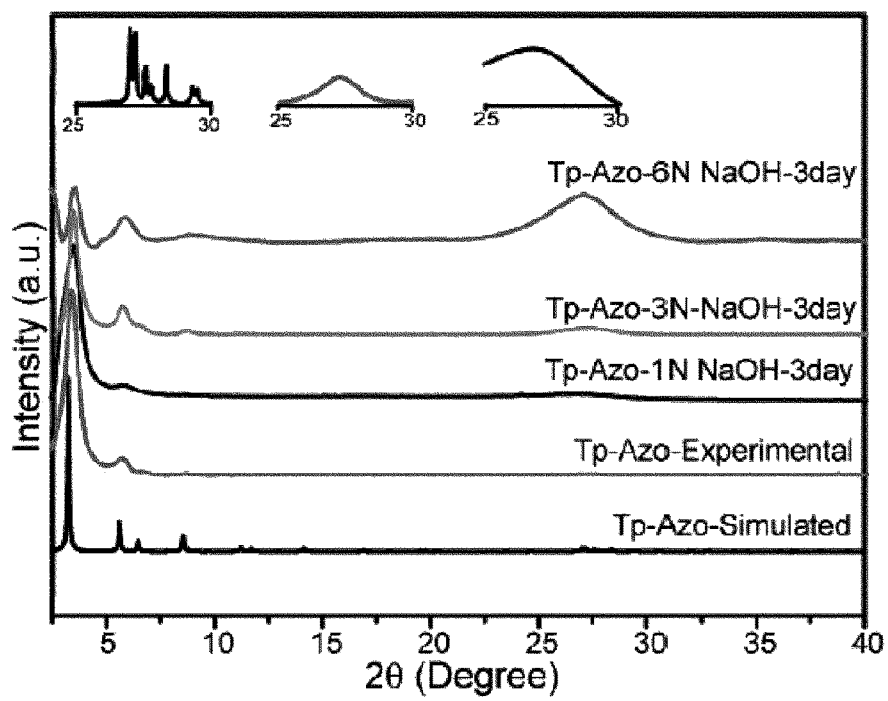
FIG. 12 is stability of Tp-Azo in base.
Figure 13:
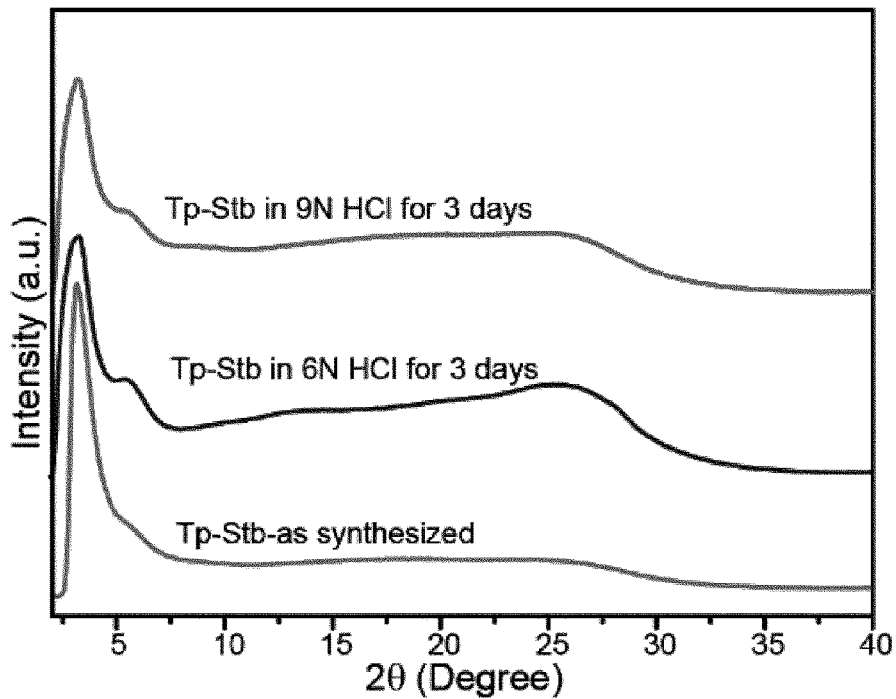
FIG. 13 is stability of Tp-Stb in acid.
Figure 14:
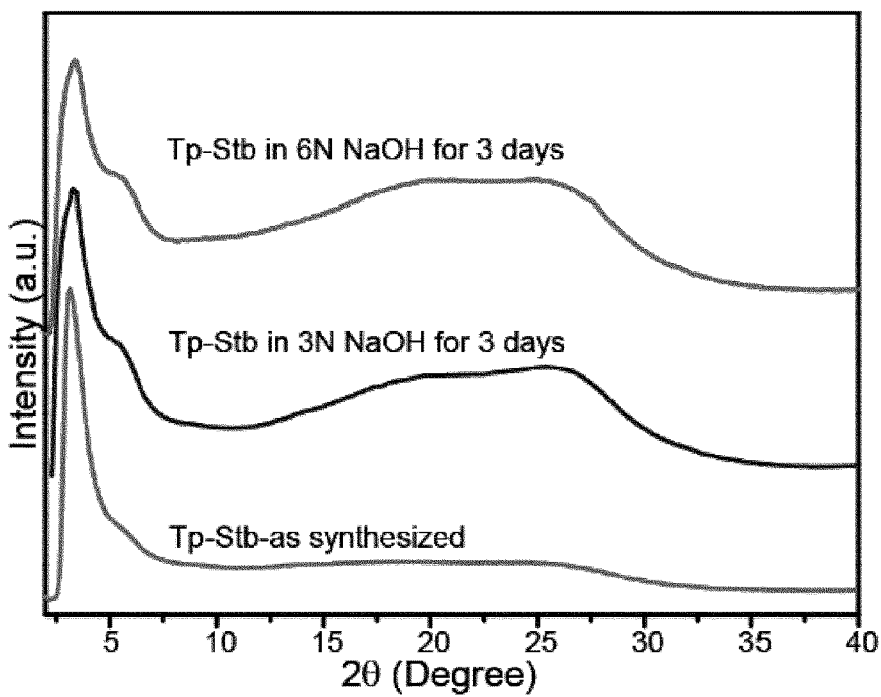
FIG. 14 is stability of Tp-Stb in base.

Further, the proton conductivities of Tp-Azo, Tp-Stb, PA@Tp-Azo and PA@Tp-Stb were measured in both hydrous (FIG. 4C) and (FIG. 4B) anhydrous condition. The conductivities are determined from the semicircles in the Nyquist plots (FIGS. 8-10). Interestingly, both Tp-Azo and Tp-Stb exhibit almost zero conductivity, which signifies that the COF backbones are acting as a support. The proton conductivity of PA@Tp-Azo and PA@Tp-Stb were measured from 295K to 415K. Conductivity values gradually increased upon heating which reaches a maximum at a temperature of 332-340 K and then decreased gradually upon increasing temperature. The proton conductivity of PA@Tp-Azo is measured as 6.7×10-5 S cm$^{-1}$ at 340K at anhydrous condition. This value is highly humidity-dependent and increases upon humidification. Finally, PA@Tp-Azo exhibit proton conductivity of 9.9×10-4 S cm$^{-1}$ at 332K under 98% relative humidity (RH). Surprisingly, PA@Tp-Stb shows almost zero proton conductivity in anhydrous condition, while exhibiting poor proton conductivity value of 2.3×10-5 S cm$^{-1}$ at 332 K under 98% RH. Notably, PA@Tp-Azo exhibit an activation energy value of 0.11 eV, which is very low when compared to Nafion (0.22 eV) and its MOF counterparts operating under humid conditions. However, Tp-Azo exhibits distinct color change (from red to black) upon $H_3PO_4$ treatment, while color of Tp-Stb remains almost unchanged (gray) upon $H_3PO_4$ loading. The UV-Visible spectra of phosphoric acid treated monomer of Tp-Azo shows a red shift of the peak from 380 nm to 496 nm due to the protonation of the azo bond.

Figure 5A:
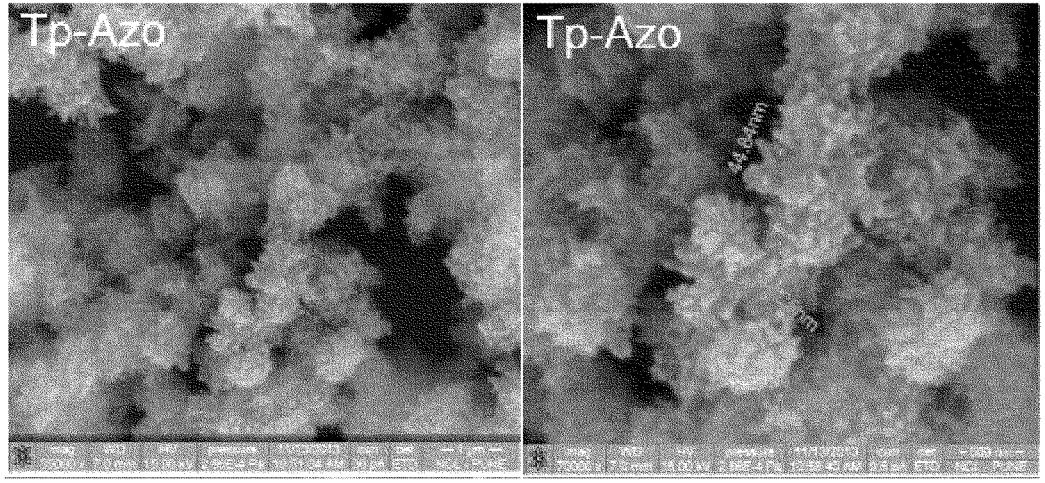
FIG. 5A is SEM images of Tp-Azo.
Figure 5B:
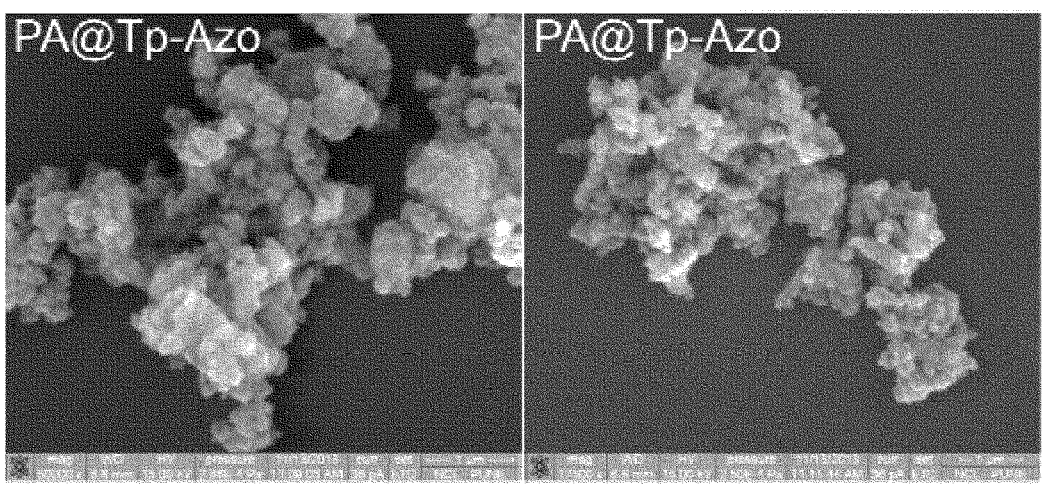
FIG. 5B is PA@Tp-Azo.
Figure 6A:
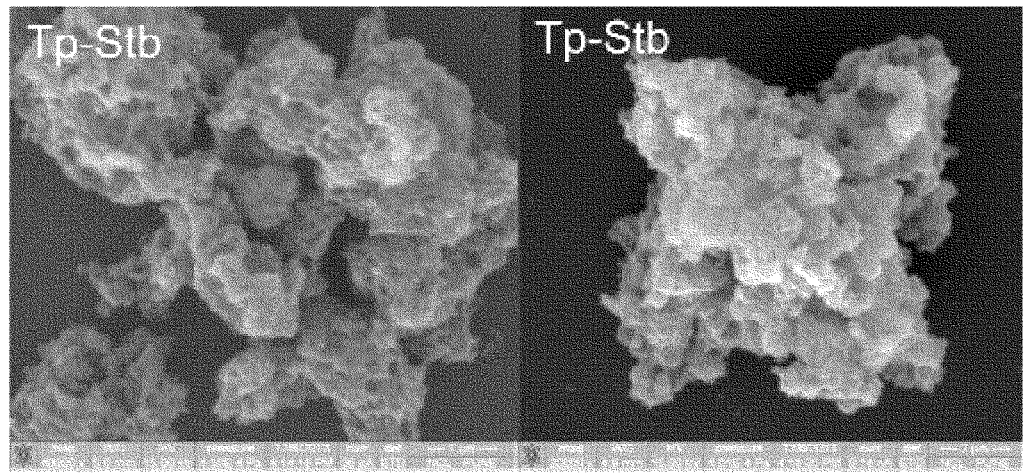
FIG. 6A is SEM images of Tp-Stb.
Figure 6B:
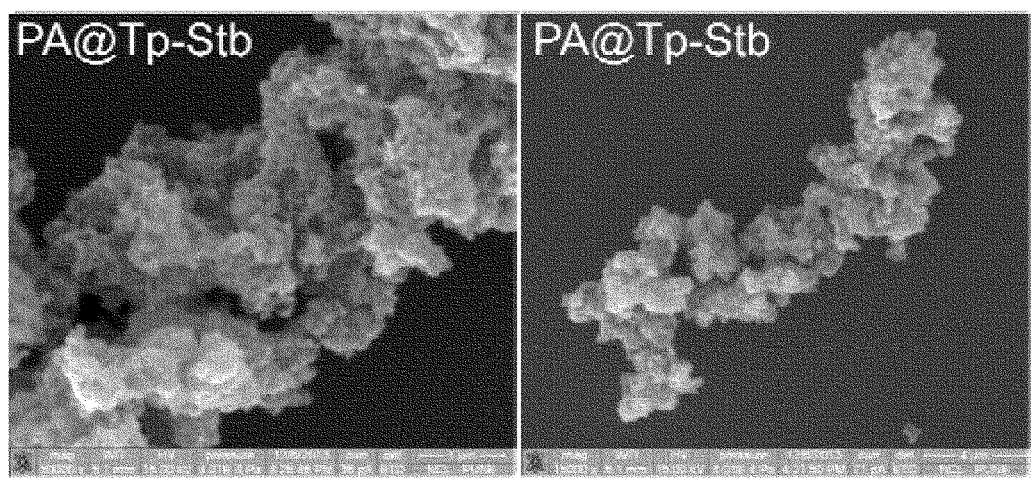
FIG. 6B is PA@Tp-Stb.
Figure 7A:
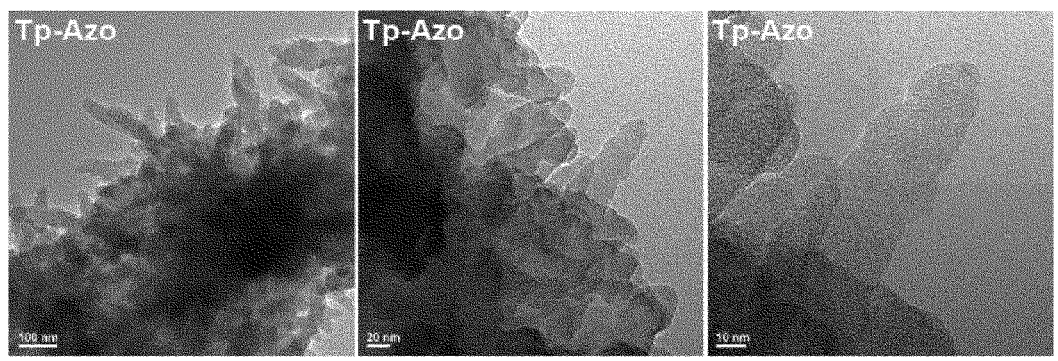
FIG. 7A is TEM images of Tp-Azo at different magnifications.
Figure 7B:
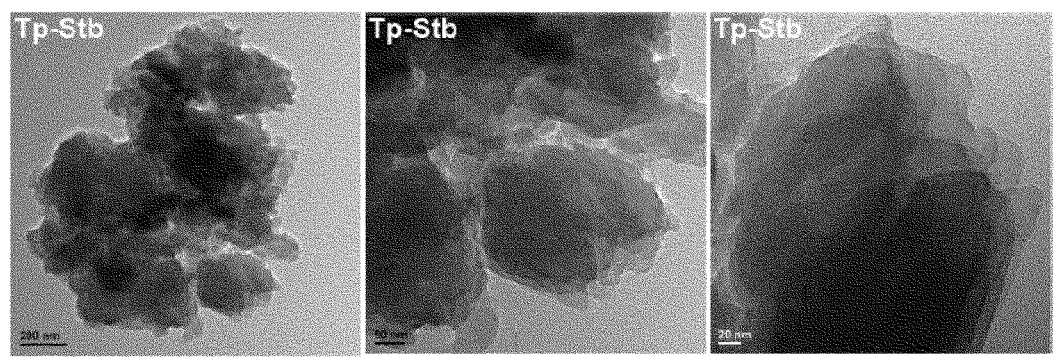
FIG. 7B is TEM images of Tp-Stb at different magnifications.

SEM (FIGS. 5, 6) and TEM (FIG. 7) images shows that Tp-Azo and Tp-Stb crystallize with a flower like morphology with aggregation of large number of petals with an average length of 40-50 nm.

EXAMPLES

Examples are given by way of illustration and therefore should not be construed to limit the scope of the invention.

Example 1: Synthesis of Tp-Azo and Tp-Stb

In the typical synthesis, a pyrex tube (o.d.×i.d.=10×8 mm$^2$ and length 18 cm) is charged with 1,3,5-triformylphloroglucinol (63 mg, 0.3 mmol) and 4,4'-azodianiline (96 mg, 0.45 mmol) or 4,4-diaminostilbene dihydrochloride (128 mg, 0.45 mmol) in (1:1) dimethylacetamide and o-dichlorobenzene as solvent (3 mL) by ultrasonication for 10 minutes and then degassed through three freeze-pump-thaw cycles. Tubes were then vacuum sealed, placed in isotherm oven for 3 days at 120° C. Finally, the material was filtered out and washed with dry acetone and dried under vacuum at 180° C. for 12 h to obtain Tp-Azo and Tp-Stb respectively.

FT-IR (Tp-Azo, powder, cm-1): 1619 (w), 1568 (s), 1450 (m), 1284 (w), 1240 (s), 1147 (s), 987 (w), 839 (m). Elemental Analysis; Anal. Calcld. For C9ON2H6: C, 68.35; H, 3.79; N, 17.72. found: C, 48.12; H, 5.27; N, 11.12. FT-IR (Tp-Stb, powder, cm-1): 1574 (s), 1518 (w), 1450 (s), 1255 (m), 991 (w), 958 (w), 824 (m). Elemental Analysis; Anal. Calcld. For C10H6ON: C, 76.92; H, 3.84; N, 8.97; found: C, 69.84; H, 4.50; N, 7.89.

Example 2: Synthesis of $H_3PO_4$ Loaded Tp-Azo and Tp-Stb (PA@Tp-Azo and PA@Tp-Stb)

PA@Tp-Azo and PA@Tp-Stb covalent organic frameworks were prepared by $H_3PO_4$ loading in Tp-Azo and Tp-Stb. The $H_3PO_4$ loading was achieved by simply immersing the evacuated COF materials (about 150 mg) as obtained in example 1 in 10 ml of 1.5 M $H_3PO_4$ for 2 h. Further, COFs were washed with copious amount of water and activated overnight (12 hr) at 353K under dynamic vacuum to obtain $H_3PO_4$ loaded PA@Tp-Azo and PA@Tp-Stb.

ADVANTAGES OF THE INVENTION

Covalent organic framework is lighter and metal free
Wide variety of functionality
Higher thermal stability
High proton-conducting ability
The highly ordered one-dimensional channels in COFs offer potential pathways for proton conduction.
The COF may be used as high-performance proton-conducting material in fuel cell applications.

While the present invention has been illustrated by description of various embodiments and while those embodiments have been described in considerable detail, it is not the intention of Applicants to restrict or in any way limit the scope of the appended claims to such details. Additional advantages and modifications will readily appear to those skilled in the art. The present invention in its broader aspects is therefore not limited to the specific details and illustrative examples shown and described. Accordingly, departures may be made from such details without departing from the spirit or scope of Applicants' invention.

What is claimed is:

1. A process for preparing phosphoric acid loaded covalent organic framework with high stability and high proton conductivity comprising steps of:
   a) dispersing 1,3,5-triformylphloroglucinol (Tp) and diamine compound in solvent by ultrasonication for 10 minutes followed by degassing the solution;
   b) heating the solution as obtained in step (a) in oven for 3-5 days at temperature in a range of 100° C. to 120° C. followed by washing and drying under vacuum at temperature in a range of 120° C. to 150° C. for period in a range of 12 h to 18 h to obtain desired covalent organic framework with at least one basic anchoring site;
   c) immersing the covalent organic framework of step (b) in $H_3PO_4$ (PA) for period in a range of 1 h to 5 h followed by washing to remove surface absorbed phosphoric acid and activating overnight for period in a range of 12 h to 18 h at temperature in a range of 60° C. to 80° C. under vacuum to obtain phosphoric acid loaded covalent organic framework.

2. The process as claimed in claim 1, wherein the diamine compound in step (a) is 4,4'-azodianiline (Azo) or 4,4-diaminostilbene (Stb) dihydrochloride.

3. The process as claimed in claim 1, wherein the covalent organic framework formed in step (b) is Tp-Azo or Tp-Stb.

4. The process as claimed in claim 1, wherein phosphoric acid loaded covalent organic framework formed in step (c) is PA@Tp-Azo or PA@Tp-Stb.

5. The process as claimed in claim 1, wherein the solvent used in step (a) is mixture of dimethylacetamide and o-dichlorobenzene in 1:1 ratio.

* * * * *